(12) United States Patent
Kaikenger et al.

(10) Patent No.: US 11,666,497 B2
(45) Date of Patent: Jun. 6, 2023

(54) SYSTEM FOR ADJUSTING THE CONFIGURATION OF A PATIENT SUPPORT APPARATUS

(71) Applicant: Hill-Rom Services, Inc., Batesville, IN (US)

(72) Inventors: Philippe Kaikenger, Pluvigner (FR);
Marion Le Gall, Vannes (FR);
Jean-Bernard Duvert, Baud (FR);
Clementine Pirio, Vannes (FR)

(73) Assignee: Hill-Rom Services, Inc., Batesville, IN (US)

( * ) Notice: Subject to any disclaimer, the term of this patent is extended or adjusted under 35 U.S.C. 154(b) by 650 days.

(21) Appl. No.: 16/655,415

(22) Filed: Oct. 17, 2019

(65) Prior Publication Data
US 2020/0121528 A1 Apr. 23, 2020

(30) Foreign Application Priority Data
Oct. 22, 2018 (EP) .................................. 18201814

(51) Int. Cl.
*A61G 7/018* (2006.01)
*A61G 7/015* (2006.01)
*G16H 40/63* (2018.01)

(52) U.S. Cl.
CPC ............. *A61G 7/018* (2013.01); *A61G 7/015* (2013.01); *G16H 40/63* (2018.01); *A61G 2203/20* (2013.01)

(58) Field of Classification Search
CPC ............................ G16H 40/63; A61G 2203/20
See application file for complete search history.

(56) References Cited

U.S. PATENT DOCUMENTS

| 4,862,529 A | 9/1989 | Peck |
| 5,398,357 A | 3/1995 | Foster |

(Continued)

FOREIGN PATENT DOCUMENTS

| CN | 1792353 A | 6/2006 |
| CN | 105433955 A | 3/2016 |

(Continued)

OTHER PUBLICATIONS

Second Chinese Office Action for Chinese Patent Application No. 201910996438.2 dated Sep. 24, 2021 and its English translation (18 pages).

(Continued)

*Primary Examiner* — Nabil H Syed
*Assistant Examiner* — Cal J Eustaquio
(74) *Attorney, Agent, or Firm* — Barnes & Thornburg LLP

(57) ABSTRACT

A system for adjusting the configuration of a patient support apparatus includes a patient support apparatus having at least one actuator configured to adjust the configuration of the patient support apparatus and a control unit to control the at least one actuator. The control unit has a memory that is configured to store patient support apparatus configurations. The control unit is also configured to: receive a first input including patient risk information of a patient to be supported; determine an optimum patient support apparatus configuration from the patient support apparatus configurations based on the patient risk information; receive a second input from a user to accept the determined optimum patient support apparatus configuration; and if the determined optimum patient support apparatus configuration is accepted by a user, control the at least one actuator to adjust the patient support apparatus into the determined optimum patient support apparatus configuration.

13 Claims, 6 Drawing Sheets

(56) References Cited

U.S. PATENT DOCUMENTS

| | | |
|---|---|---|
| 5,454,126 A | 10/1995 | Foster et al. |
| 5,479,666 A | 1/1996 | Foster et al. |
| 5,715,548 A | 2/1998 | Weismiller et al. |
| 6,163,903 A | 12/2000 | Weismiller et al. |
| 6,336,235 B1 | 1/2002 | Ruehl |
| 6,854,141 B2 | 2/2005 | Nagaoka et al. |
| 6,870,341 B2 | 3/2005 | Nagaoka et al. |
| 6,957,458 B2 | 10/2005 | Nagaoka et al. |
| 6,957,459 B2 | 10/2005 | Nagaoka et al. |
| 7,058,999 B2 | 6/2006 | Horitani et al. |
| 7,174,586 B2 | 2/2007 | Nagaoka |
| 7,458,119 B2 | 12/2008 | Hornbach et al. |
| 8,048,005 B2 | 11/2011 | Dixon et al. |
| 8,065,024 B2 | 11/2011 | Nagaoka et al. |
| 8,068,924 B2 | 11/2011 | Nagaoka et al. |
| 8,381,336 B2 | 2/2013 | Kazuno et al. |
| 8,413,273 B2 | 4/2013 | Hornbach et al. |
| 8,474,072 B2 | 7/2013 | O'Keefe et al. |
| 8,499,385 B2 | 8/2013 | Horitani |
| 8,640,285 B2 | 2/2014 | Heimbrock et al. |
| 8,689,376 B2 | 4/2014 | Becker et al. |
| 8,838,411 B2 | 9/2014 | Kazuno et al. |
| 8,844,076 B2 | 9/2014 | Becker et al. |
| 8,844,078 B2 | 9/2014 | Hornbach et al. |
| 9,149,190 B2 | 10/2015 | Mayoras, Jr. |
| 9,149,403 B2 | 10/2015 | Turner et al. |
| 9,198,519 B2 | 12/2015 | Katoh et al. |
| 9,198,815 B2 | 12/2015 | Murai |
| 9,320,662 B2 | 4/2016 | Hayes et al. |
| 9,504,619 B2 | 11/2016 | Murai |
| 9,930,969 B2 | 4/2018 | Shimada et al. |
| 10,111,791 B2 | 10/2018 | Murai |
| 10,201,466 B2 | 2/2019 | Shimada et al. |
| 10,272,007 B2 | 4/2019 | Turner et al. |
| 10,413,462 B2 | 9/2019 | Shimada et al. |
| 10,420,517 B2 | 9/2019 | Mayoras, Jr. |
| 10,463,552 B2 | 11/2019 | Murai |
| 2007/0174965 A1* | 8/2007 | Lemire ............ A61G 7/0528 5/630 |
| 2008/0172789 A1* | 7/2008 | Elliot ............... A61G 7/0527 5/616 |
| 2009/0275808 A1* | 11/2009 | DiMaio ............ A61G 7/05769 128/845 |
| 2014/0012510 A1* | 1/2014 | Mensinger ......... G16H 40/67 702/19 |
| 2016/0367170 A1 | 12/2016 | Larson et al. |
| 2019/0029900 A1 | 1/2019 | Walton et al. |
| 2019/0083353 A1* | 3/2019 | Khurana ............ A61B 5/0285 |

FOREIGN PATENT DOCUMENTS

| | | |
|---|---|---|
| CN | 206334042 A | 7/2017 |
| CN | 107049654 A | 8/2017 |
| EP | 2260755 A1 | 12/2010 |
| EP | 3207911 A1 | 8/2017 |
| GN | 101815491 A | 8/2010 |
| WO | 2011113070 A1 | 9/2011 |

OTHER PUBLICATIONS

Office Action dated Feb. 20, 2021, issued by the Chinese Patent Office in Chinese Patent Application No. 2019109964382 and its English translation.

Extended European Search Report for European Patent Application No. 18201814.3 dated May 27, 2019; 6 pages.

* cited by examiner

SYSTEM FOR ADJUSTING THE CONFIGURATION OF A PATIENT SUPPORT APPARATUS

The present application claims priority, under 35 U.S.C. § 119(a), of European Application No. 18201814.3 which was filed Oct. 22, 2018 and which is hereby incorporated by reference herein.

TECHNICAL FIELD

The present disclosure relates to a system for adjusting the configuration of a patient support apparatus.

BACKGROUND

A patient support apparatus, such as a stretcher, a hospital bed, or a similar device, may be used to support a person in a number of different positions, including a laying down position or a seated position. Such a product may be found, for example, in healthcare facilities, homes, and/or other locations in which patient care is provided. Known patient support apparatuses may include actuators that enable the position or configuration of the patient support apparatus to be adjusted.

Known patient support apparatuses may also comprise a control unit which can be used to control these adjustments, move a frame of a patient support apparatus to a particular position, and adjust a mattress or therapy setting in response to a user input. For example, Hill-Rom's TOTALCARE® and PROGRESSA® beds have a chair egress position.

Known patient support apparatuses may either be adjusted manually, or adjusted automatically based on given patient information. Manual control of the configuration of a patient support apparatus provides full control to a user to ensure minimum patient risk. Automation of adjustment may be advantageous in many situations. However, automation of the adjustment process may result in increased risk to a patient.

SUMMARY

Some embodiments of the invention in some of its various aspects may be defined in the independent claims below to which reference should now be made. Optional features are set forth in the dependent claims.

The inventors of the embodiments of the present disclosure have appreciated the need for a patient support apparatus system which can be adjusted by a control unit while maintaining patient safety.

According to a first aspect of the present disclosure, there is provided a system for adjusting the configuration of a patient support apparatus, the system comprising: a patient support apparatus comprising at least one actuator configured to adjust the configuration of the patient support apparatus; and a control unit configured to control the at least one actuator, the control unit comprising a memory, the memory configured to store a plurality of patient support apparatus configurations; characterised in that the control unit is configured to: receive a first input comprising patient risk information of a patient to be supported; determine an optimum patient support apparatus configuration from the plurality of patient support apparatus configurations based on the patient risk information; receive a second input from a user to accept the determined optimum patient support apparatus configuration; and if the determined optimum patient support apparatus configuration is accepted by a user, control the at least one actuator to adjust the patient support apparatus into the determined optimum patient support apparatus configuration.

An example system for adjusting the configuration of a patient support apparatus comprises a bed apparatus and a control unit such a man-machine interface or computer on which a user may input patient risk information. The control unit determines and suggests an optimum patient support apparatus configuration, which a user may then accept, decline, or modify. If the user accepts the optimum configuration, the control unit controls actuators to adjust the patient support apparatus to the optimum configuration.

The patient support apparatus may be a hospital bed. The patient support apparatus comprises at least one actuator configured to adjust the configuration of the patient support apparatus.

The patient support apparatus may comprise a plurality of portions. The at least one actuator may be configured to control the position, height, and/or angle of the plurality of portions. Each actuator may control one or more of the plurality of portions.

The system also comprises a control unit configured to control the at least one actuator. The control unit may be a computer device separate to, but in communication connection with, the patient support apparatus, or the control unit may be a man-machine interface attached to the patient support apparatus. The control unit may comprise a user interface and one or more of the inputs may be input by a user through the user interface. The control unit also comprises a memory which is configured to store a plurality of patient support apparatus configurations. The memory may comprise a local hard drive. The memory may comprise a cloud storage system. The patient support apparatus configurations may include positions of the patient support apparatus, such as the height and angle of each portion of a patient support apparatus.

The control unit is configured to receive a first input comprising patient risk information of a patient to be supported. The input may be input by a user inputting information into the control unit. Alternatively, the patient risk information may be input by a hospital records system directly to the control unit, without the requirement of a user inputting the information. The patient risk information may comprise one or more of the pulmonary risk of the patient, the vascular risk of the patient, and the pressure ulcer risk of the patient. If the patient is at risk of a pressure ulcer, the patient risk information may further comprise one or more of: the body mass index (BMI) of the patient, wound location information, and information about whether the patient can tolerate an alternating low pressure (ALP) mode for a mattress.

The control unit is also configured to determine an optimum patient support apparatus configuration from the plurality of patient support apparatus configurations based on the patient risk information. Once input, the information may be processed in order to determine an optimum patient support apparatus configuration. The control unit may process the information locally. Alternatively or in addition, the information may be processed on a processor separate to the system or in a cloud configuration and then returned to the control unit. The patient risk information is analyzed and an optimum patient support apparatus may be chosen which results in the lowest risk to the patient. Examples of such determined optimum patient support apparatus configurations may include: in a case of pulmonary risk, the bed backrest may be articulated in between 45 degrees>bed backrest angle>30 degrees and/or Continuous Lateral Rotation Therapy (CLRT) may be used; in a case of vascular issues, a cardiac chair configuration is recommended; in the case of a pressure ulcer, Lateral Pressure Redistribution (LPR) may replace the existing manual turn protocol, and/or a flat configuration may be recommended to optimize pressure distribution. The optimum patient support apparatus configuration may also comprise turning the patient alternatively from left supine right. In the case of a combination of issues, the optimum configuration will be determined to optimally address all the risks.

The control unit is also configured to receive a second input from a user to accept the determined optimum patient support apparatus configuration. The control unit may be configured to display the determined optimum configuration before receiving the second input from a user. Alternatively or in addition, the control unit may indicate the determined optimum configuration in another manner such as with an audio indication or control another device or computer to display the determined configuration. The user may then consider the determined configuration. The control unit or user interface may then be used by the user to provide the second input to accept or not accept the determined configuration. Alternatively, the second input received by the control unit may be input by a user through an electronic terminal. The electronic terminal may be an electronic device such as a mobile phone or tablet device separate to the patient support apparatus, which may be more convenient for a user. The electronic device may be in communication connection with the control unit, for example via near field communication, a Bluetooth connection, or a local Wi-Fi connection. The input to accept or not accept the determined configuration may be a single input so to provide a more convenient and quicker process for a user and the patient. In other words, conveniently, a one-click activation may be provided that can achieve all combinations of settings and configurations.

The control unit is also configured to control the at least one actuator to adjust the patient support apparatus into the determined optimum patient support apparatus configuration if the determined optimum patient support apparatus configuration is accepted by a user.

If the determined optimum patient support apparatus configuration is not accepted by a user, the control unit may be further configured to receive a third input by a user to modify the patient support apparatus configuration and control the at least one actuator to adjust the patient support apparatus based on the third input. For example, the user may adjust the angle or height of a portion of the hospital bed.

The patient support apparatus may further comprise a patient support surface for supporting the patient and the at least one actuator is configured to adjust the configuration of the patient support surface. The patient support surface may comprise a plurality of sections and the at least one actuator may be configured to adjust the position and angle of the plurality of sections relative to each other. The stored patient support apparatus configurations may comprise relative positions of the plurality of sections relative to each other.

The patient support apparatus may comprise a therapy mattress. The patient support apparatus configurations may comprise therapy mattress settings. The therapy mattress settings may comprise a continuous low pressure (CLP) sequence and an alternating low pressure (ALP) sequence. An alternating low pressure (or dynamic) sequence involves alternating inflation and deflation between bladders in the mattress in order to locally load and unload parts of the patient. However, some patients experience sickness during this process and therefore only certain patients can tolerate ALP mode. A combination of information regarding the patient's BMI and ALP tolerance may aid the control unit in determining a CLP or ALP setting proposal.

According to an aspect of the present disclosure, there is provided a method for adjusting the configuration of a patient support apparatus. The method comprises: receiving at a control unit a first input comprising patient risk information of a patient to be supported; determining an optimum patient support apparatus configuration from a plurality of patient support apparatus configurations stored in a memory of the control unit based on the patient risk information; receiving at the control unit a second input from a user to accept the determined optimum patient support apparatus configuration; and if the determined optimum patient support apparatus configuration is accepted by a user, controlling by the control unit the at least one actuator to adjust the patient support apparatus into the determined optimum patient support apparatus configuration.

BRIEF DESCRIPTION OF THE DRAWINGS

The embodiments of the present disclosure will be described in more detail, by way of example, with reference to the accompanying drawings in which:

FIG. 2b is a perspective view of the patient support apparatus of FIG. 2a;

FIG. 4b is a perspective view of the control unit of FIG. 4a;

FIG. 4c is a perspective view of the patient support apparatus of FIG. 4a; and

Like features of the drawings are denoted by like reference numerals.

DETAILED DESCRIPTION

Figure 1:
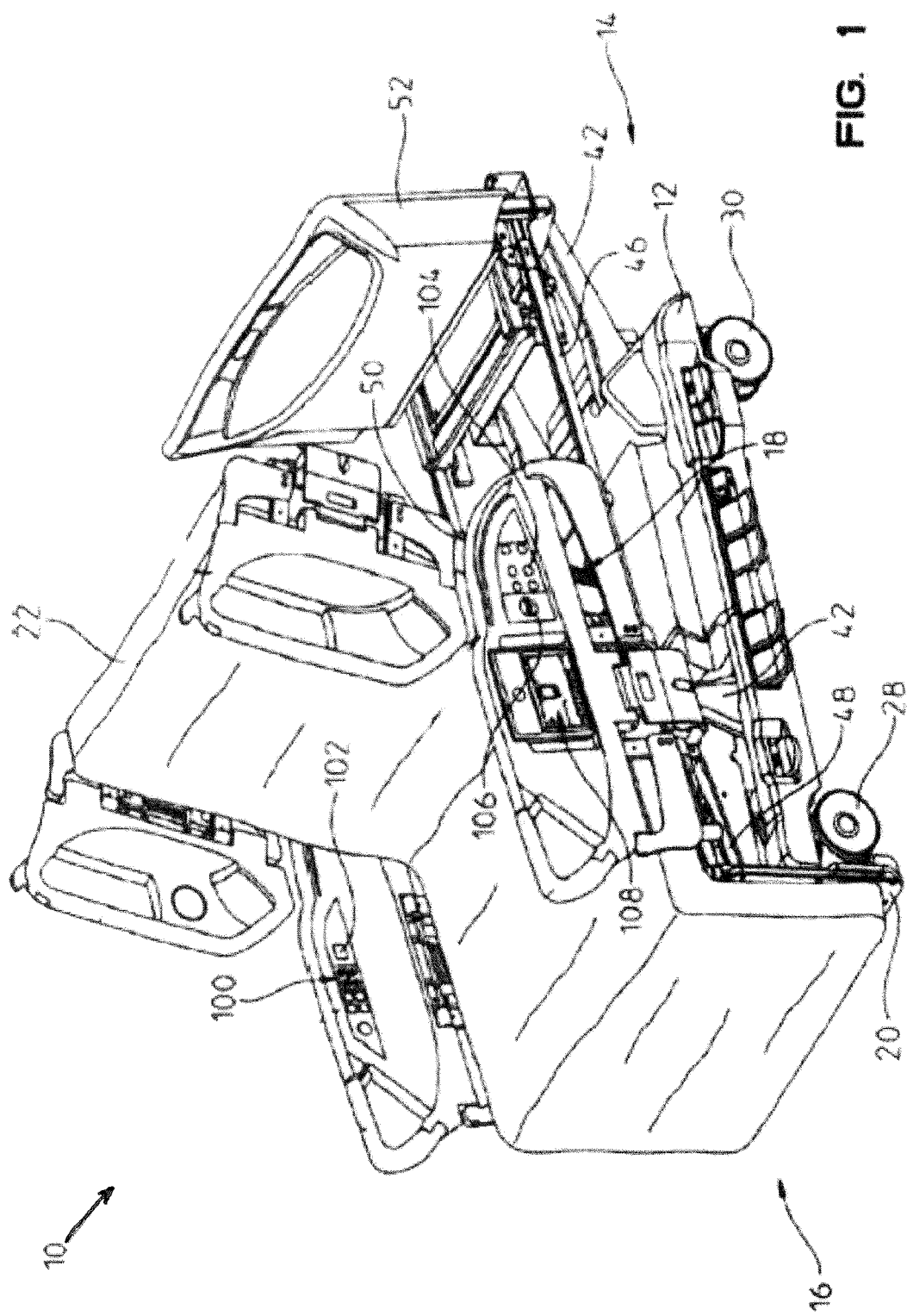
FIG. 1 is a perspective view of a known patient support apparatus.

FIG. 1 illustrates a known patient support apparatus 10, which in this example is a hospital bed 10. The hospital bed is a type typically used in hospitals and other facilities in which health care is provided, but aspects of the present disclosure are applicable to any type of bed or similar patient support apparatus.

The hospital bed 10 may assume a number of configurations, such as a flat or horizontal position. FIG. 1 illustrates the bed in a chair configuration. The hospital bed 10 includes a base 12, which has a head end 14 and a foot end 16 spaced from the head end 14. The base 12 is supported by a number of casters 28, 30. The casters 28, 30 may have an electronically or mechanically controlled brake and/or steer lock mechanism coupled thereto.

A frame 46 is coupled to and supported by the base 12. A lift mechanism, which includes lift arms 42, is configured to raise, lower, and tilt the frame 46 relative to the base 12.

A patient support surface 18 is coupled to and supported by the frame 46. The patient support surface 18 is configured to support a therapy mattress 22, which is configured to support a patient. The patient support surface has a plurality of sections including a foot section 20, a head section 50, and a torso section 48. The torso section further includes a separate thigh section and a seat section. The foot section 20 and the head section 50 are pivotable, such that the patient support surface may assume a number of different positions as noted above.

While not visible in FIG. 1, the hospital bed 10 comprises at least one actuator, and in this example the bed comprises a plurality of actuators. In this example, the actuators are hydraulic actuators, but they may be electric linear actuators. The actuators enable the bed to assume different positions. In this example, the actuators are coupled to the frame 46 to enable raising, lowering, and tilting of the frame 46 relative to the base 12. Separate actuators are coupled to each of the sections of the patient support surface 20, 50, 48 to enable pivoting of the sections.

The hospital bed comprises controllers 100, 102, 104, 106, 108 to enable a user to control the position of the sections 20, 50, 48 of the patient support surface 18 as well as control the mattress setting.

Figure 2A:
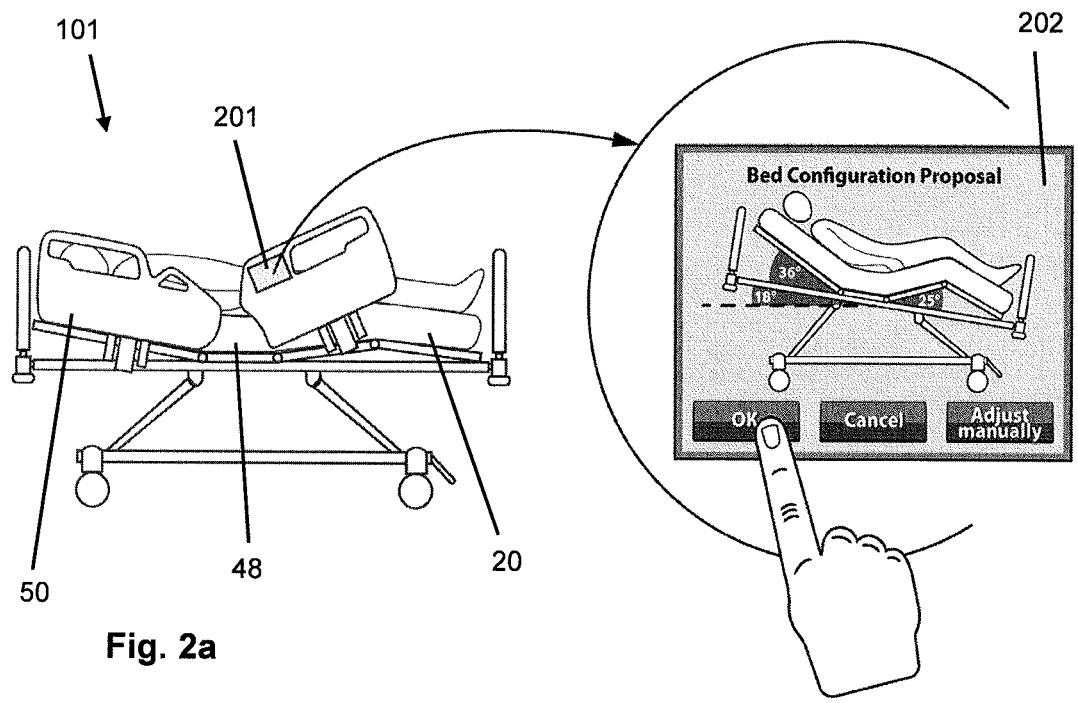
FIG. 2a is a perspective view of a patient support apparatus and a control unit embodying an aspect of the present disclosure.

FIG. 2a illustrates a patient support apparatus 101 which is similar in most respects to the patient support apparatus illustrated in FIG. 1, but significantly, the patient support apparatus 101 further comprises a control unit 201, also illustrated in detail in FIG. 2a. In this example, the control unit 201 comprises a touch screen user interface 202 built into the patient support apparatus frame allowing for convenient access by a user. The touch screen provides the user interface for a user to provide one or more inputs to the control unit 201. FIG. 2a illustrates the patient support apparatus 101 in a first position and FIG. 2b illustrates the patient support apparatus in a second position.

Figure 2B:
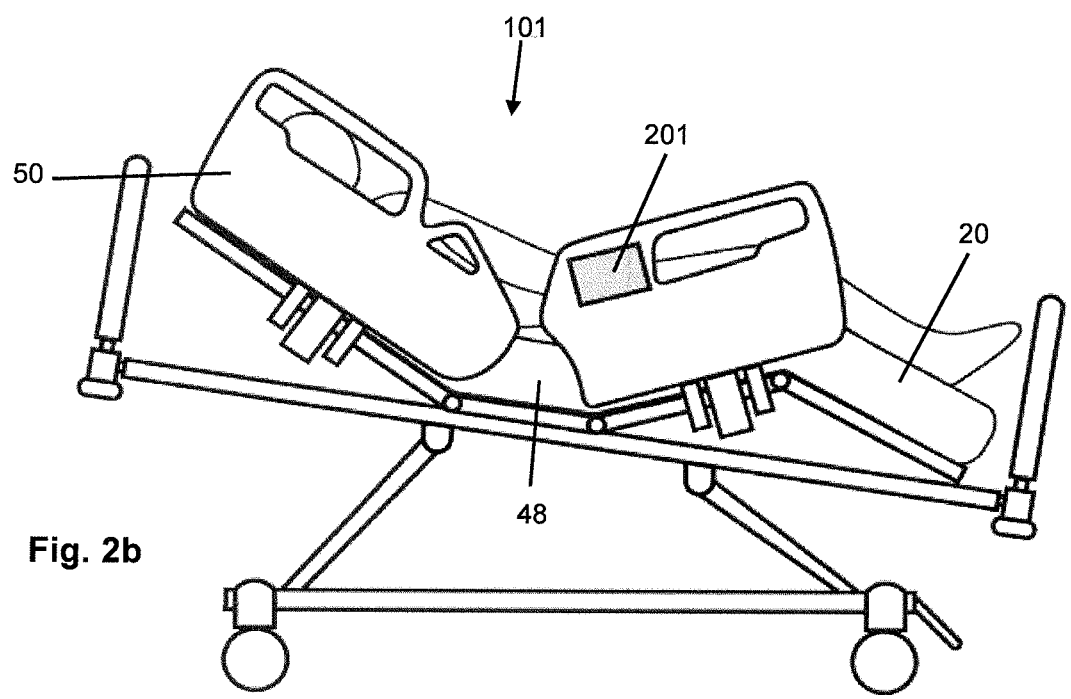
Figure 3:
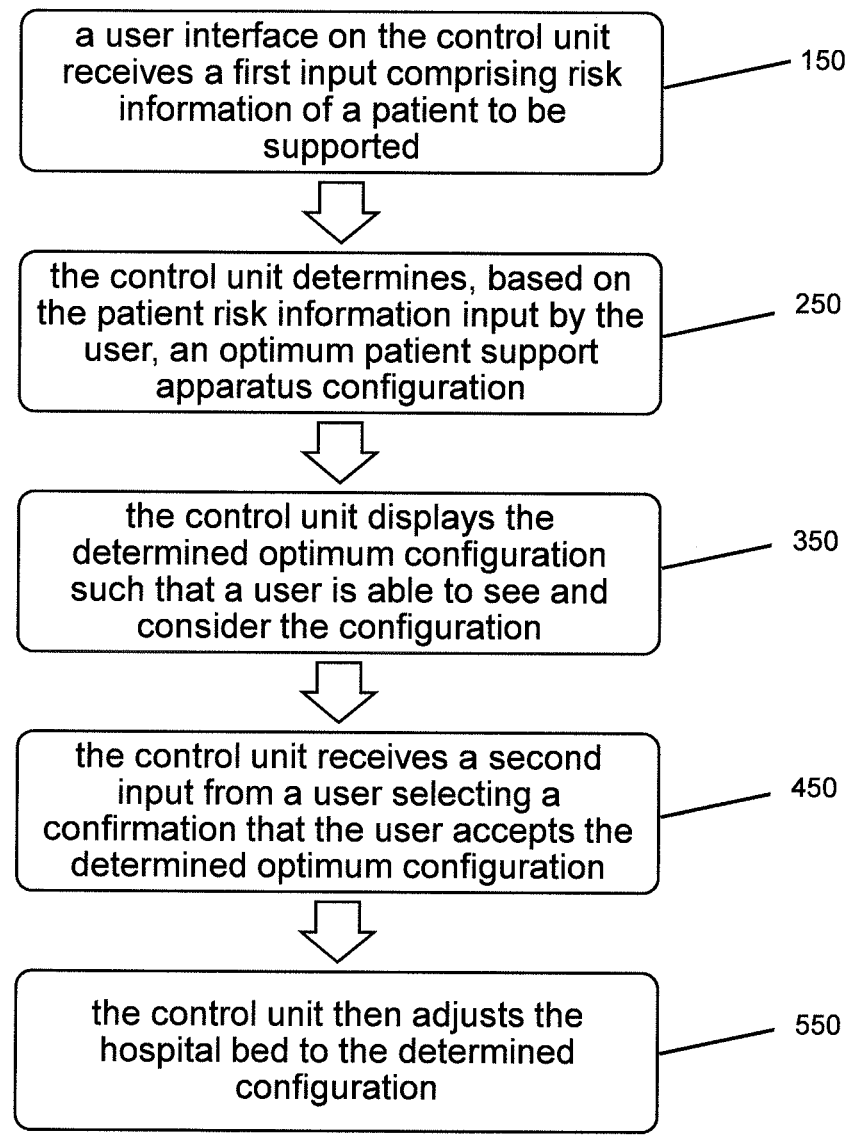
FIG. 3 is a flow diagram illustrating an aspect of the present disclosure.

FIG. 3 is a flow diagram illustrating the process of adjusting the patient support apparatus 101 illustrated by FIGS. 2a and 2b. The process will now be described with reference to FIGS. 2a, FIG. 2b, and FIG. 4.

At step 150 of FIG. 3, a user interface 202 on the control unit 201 receives a first input (not shown) comprising risk information of a patient to be supported. The risk information comprises pulmonary risk, vascular risk, and risk of a pressure ulcer. The patient risk information therefore further comprises the BMI of the patient, the wound location information, and whether or not the patient can tolerate an alternating low pressure mode of a therapy mattress.

At step 250 of FIG. 3, the control unit determines, based on the patient risk information input by the user, an optimum patient support apparatus configuration. To do this, the processor of the control unit performs analysis of the patient risk information and compares the information to look up tables stored in the memory of the control unit and selects an optimum configuration from the plurality of stored configurations in the memory of the control unit. These include bed articulation such as the positions of the plurality of sections 20, 50, 48. The stored configurations also include a therapy setting for the therapy mattress. In this example the therapy setting is a CLP setting.

At step 350 of FIG. 3, the control unit displays the determined optimum configuration such that a user is able to see and consider the configuration, as illustrated in FIG. 2a. In this example, the user is a healthcare professional and therefor is able to assess the safety risks and benefits of the determined configuration. Significantly, rather than the control unit automatically adjusting the hospital bed to the determined configuration, the present system includes a human assessment of the determined configuration, which may take into account factors that cannot be included in the inputted patient risk information. In this example, the control unit also displays three input options in the form of touch inputs including: an indication that the user accepts the determined configuration, an indication that the user denies the determined configuration, and an indication that the user wishes to modify the determined configuration.

As illustrated in FIG. 2a and at step 450 of FIG. 3, the control unit receives a second input from a user. In this example, the second input is input by the user through the touch screen user interface 202 on the control unit 201. The second input provides an indication to the control unit whether the user accepts the determined configuration or not. In this example, the second input is a single touch operation from the user, selecting a confirmation that the user accepts the determined optimum configuration.

At step 550 of FIG. 3, the control unit has received the second input from a user indicating that the determined configuration has been accepted. As illustrated in FIG. 2b, the control unit then adjusts the hospital bed to the determined configuration, or a second configuration, including the articulation of the sections of the patient support surface and the therapy mattress setting.

Alternatively, FIGS. 4a to 4c, and 5 illustrate a process in which the determined configuration is not accepted by a user. Here, the process begins in the same way as the process illustrated by FIG. 3.

Figure 4A:
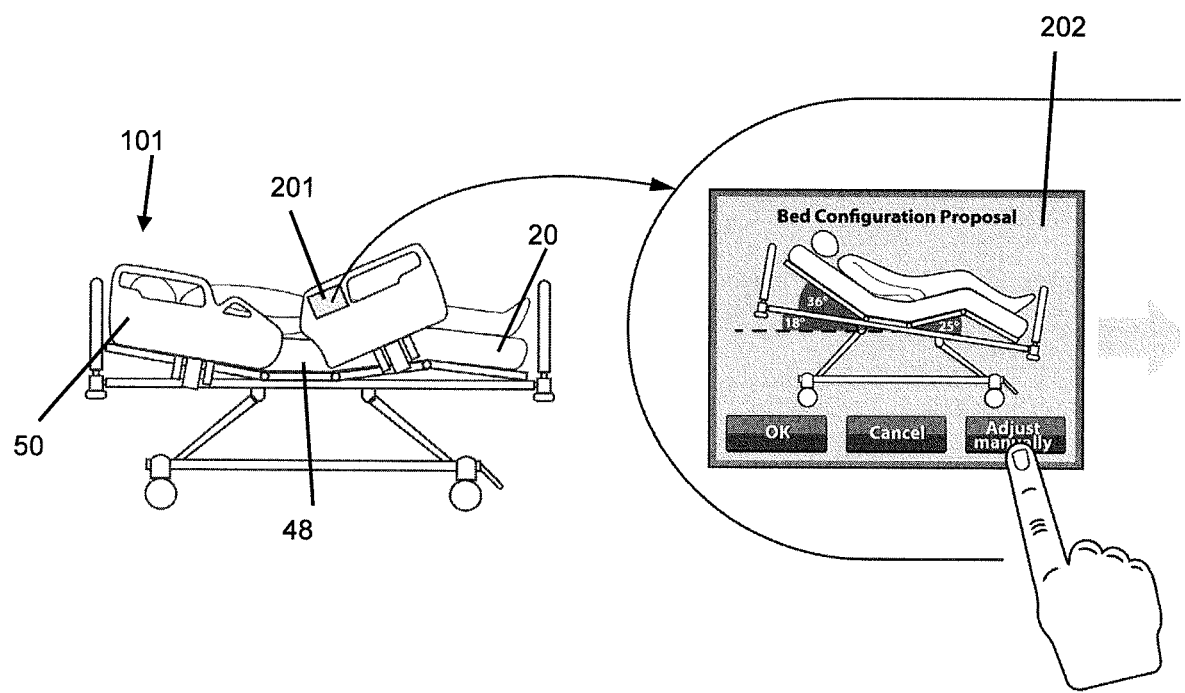
FIG. 4a is a perspective view of a patient support apparatus and a control unit embodying an aspect of the present disclosure.
Figure 5:
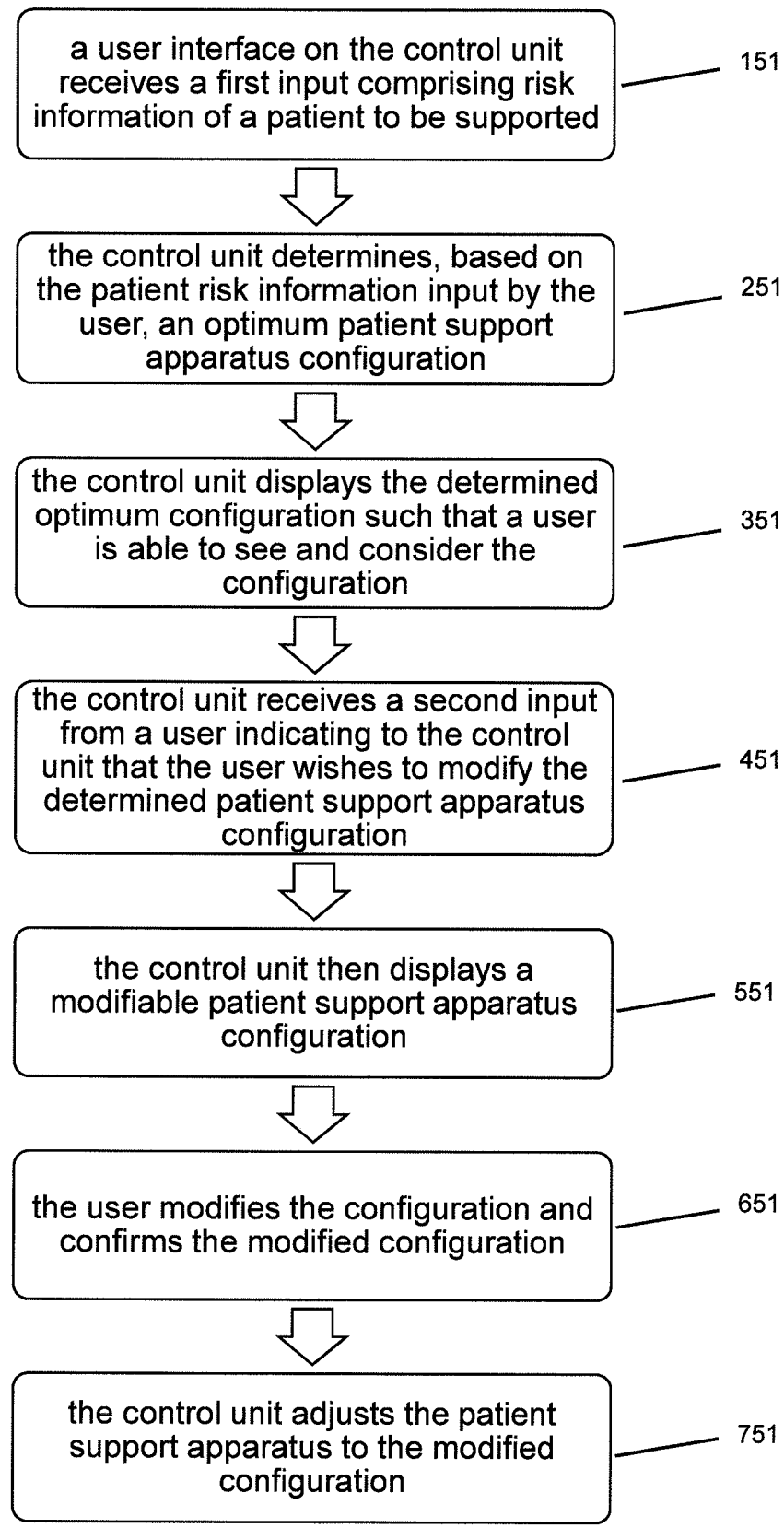
FIG. 5 is a flow diagram illustrating an aspect of the present disclosure.

At step 151 of FIG. 5, the user interface 202 on the control unit 201 receives a first input comprising risk information of a patient to be supported and the control unit 201 determines an optimum patient support apparatus configuration based on the patient risk information as illustrated at step 251. At step 351 of FIG. 5 and illustrated at FIG. 4a, the control unit displays the determined patient support apparatus and three input options.

Figure 4B:
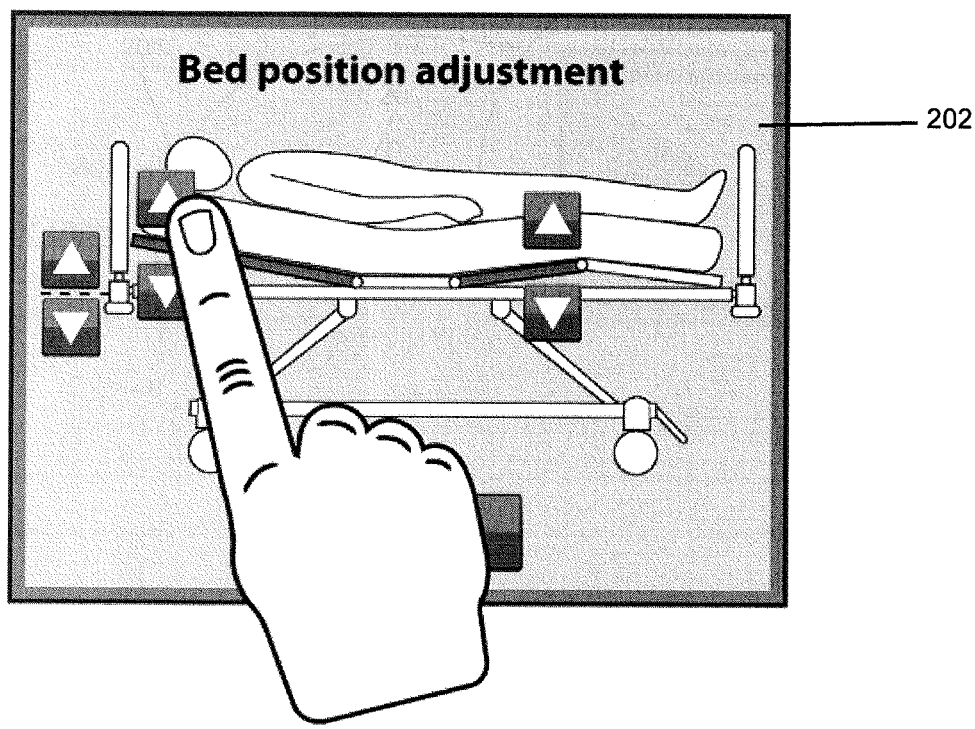

At step 451 and as illustrated at FIG. 4a, the control unit receives a second input from a user. The second input is input by the user through the touch screen user interface 202 on the control unit 201 by a single touch operation. In this example, the second input provides an indication to the control unit that the user wishes to modify the determined patient support apparatus configuration. As illustrated by FIG. 4b and at step 551, the control unit then displays a modifiable patient support apparatus configuration. In this example, the configuration is modifiable by touch input operations performed on the user interface of the control unit to adjust the height and angle of each portion of the patient support apparatus, as well as the therapy mattress setting.

At step 651 of FIG. 5, once the user has modified the configuration, another input is entered to confirm the modified configuration.

Figure 4C:
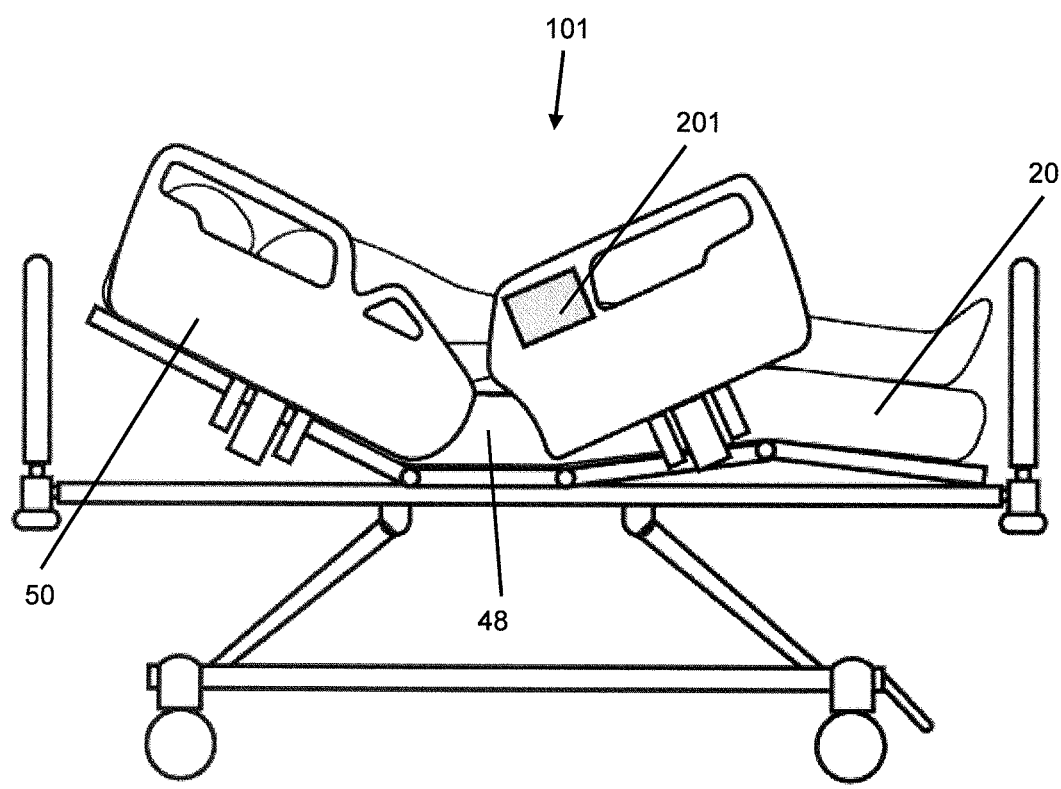

At step 751, the control unit adjusts the patient support apparatus to the modified configuration, as illustrated at FIG. 4c.

Embodiments contemplated by the present disclosure have been described. It will be appreciated that variations and modifications may be made to the described embodiments within the scope of the present disclosure. For example, alternatively, the user may not accept or modify the determined configuration. The user may also be given the opportunity to override the configuration entirely and select a new combination of settings for a new configuration. In this way, the user is given full control over the configuration before the control unit adjusts the bed, increasing the safety of the apparatus.

Additionally, the user may provide the second input through a mobile phone electronic device. The mobile phone is in communication connection with the control unit via a wireless connection which in this example is a local Wi-Fi connection, allowing the user to accept, modify, or deny a determined configuration. In this example, the user can also use the mobile electronic device to input patient risk information or manually adjust the patient support apparatus or therapy mattress setting.

The invention claimed is:

1. A system for adjusting the configuration of a patient support apparatus, the system comprising:
   a patient support apparatus comprising at least one actuator configured to adjust the configuration of the patient support apparatus; and
   a control unit configured to control the at least one actuator, the control unit comprising a memory, the memory configured to store a plurality of patient support apparatus configurations each of which corresponds to a unique set of physical positions of a plurality of frame elements of a frame of the patient support apparatus; wherein the control unit is configured to:
   receive a first input comprising patient risk information of a patient to be supported, wherein the first input comprising patient risk information is input by a user manually via inputs of the patient support apparatus or is communicated to the patient support apparatus from a hospital records system;
   determine an optimum patient support apparatus configuration from among the plurality of patient support apparatus configurations based on the patient risk information;
   display the determined optimum patient support apparatus configuration to the user;
   receive a second input that is entered manually by the user to accept the determined optimum patient support apparatus configuration; and
   if the determined optimum patient support apparatus configuration is accepted by the user, control the at least one actuator to adjust the frame elements of the frame of the patient support apparatus into the determined optimum patient support apparatus configuration;
   wherein if the determined optimum patient support apparatus configuration is not accepted by the user, the control unit is further configured to receive a third input that is entered manually by the user to modify the displayed optimum patient support apparatus configuration into a modified patient support apparatus configuration that is displayed to the user, and thereafter to control the at least one actuator to adjust the frame elements of the frame of the patient support apparatus into the modified patient support apparatus configuration in response to a fourth user input that is entered manually by the user;
   wherein the second input from the user to accept the determined optimum patient support apparatus configuration is a single input; and
   wherein the electronic terminal is a mobile telephone or tablet device or desktop device separate to the patient support apparatus.

2. The system of claim 1, wherein the control unit is further configured to display the determined optimum patient support apparatus configuration on a graphical user interface of the patient support apparatus before receiving the second input from the user.

3. The system of claim 1, wherein the third input by the user to modify the patient support apparatus configuration comprises an arrow icon associated with a corresponding one of the frame elements as displayed.

4. The system of claim 1, wherein the patient risk information includes one or more of: a pulmonary risk of the patient, a vascular risk of the patient, or a pressure ulcer risk of the patient.

5. The system of claim 4, wherein if the patient is at risk of a pressure ulcer, the patient risk information further comprises one or more of: the body mass index (BMI) of the patient, wound location information, or information about whether the patient can tolerate an alternating low pressure (ALP) mode for a mattress.

6. The system of claim 1, wherein the patient support apparatus further comprises a patient support surface for supporting the patient and the at least one actuator is configured to adjust the configuration of the patient support surface.

7. The system of claim 6, wherein the patient support surface comprises a plurality of sections and the at least one actuator is configured to adjust the position and angle of the plurality of sections relative to each other.

8. The system of claim 7, wherein the stored patient support apparatus configurations comprise relative positions of the plurality of sections.

9. The system of claim 1, wherein the patient support apparatus comprises a therapy mattress.

10. The system of claim 9, wherein the stored patient support apparatus configurations comprise therapy mattress settings.

11. The system of claim 10, wherein the therapy mattress settings comprise a continuous low pressure sequence or an alternating low pressure sequence.

12. The system of claim 1, wherein the control unit further comprises a user interface and one or more of the first and second inputs is input by the user through the user interface.

13. The system of claim 1, wherein the second input received by the control unit is input by the user through an electronic terminal.

* * * * *